(12) United States Patent
Ishibashi et al.

(10) Patent No.: US 8,722,065 B2
(45) Date of Patent: May 13, 2014

(54) LIDOCAINE TAPE PREPARATION

(75) Inventors: Masaki Ishibashi, Higashikagawa (JP);
Hidetoshi Hamamoto, Higashikagawa (JP)

(73) Assignee: MEDRx Co., Ltd., Kagawa (JP)

( * ) Notice: Subject to any disclaimer, the term of this patent is extended or adjusted under 35 U.S.C. 154(b) by 0 days.

(21) Appl. No.: 12/734,583

(22) PCT Filed: Nov. 10, 2008

(86) PCT No.: PCT/JP2008/003242
§ 371 (c)(1),
(2), (4) Date: May 11, 2010

(87) PCT Pub. No.: WO2009/060629
PCT Pub. Date: May 14, 2009

(65) Prior Publication Data
US 2010/0234471 A1     Sep. 16, 2010

(30) Foreign Application Priority Data
Nov. 11, 2007   (JP) .................................. 2007-292663

(51) Int. Cl.
*A61K 9/00*     (2006.01)

(52) U.S. Cl.
USPC ....................................................... 424/400

(58) Field of Classification Search
USPC ....................................................... 424/400
See application file for complete search history.

(56) References Cited

U.S. PATENT DOCUMENTS

| | | | |
|---|---|---|---|
| 5,059,189 A * | 10/1991 | Cilento et al. ................ | 604/307 |
| 5,658,559 A * | 8/1997 | Smith ........................ | 424/78.02 |
| 2003/0130636 A1 * | 7/2003 | Brock et al. ................. | 604/367 |

FOREIGN PATENT DOCUMENTS

| | | |
|---|---|---|
| JP | 3-90023 | 4/1991 |
| JP | 6-040947 | 2/1994 |
| JP | 07-215850 | 8/1995 |
| JP | 10-316590 | 12/1998 |
| JP | 11-049670 | 2/1999 |
| JP | 2006328059 | * 12/2006 |
| RO | 108413 | 5/1994 |
| WO | 2005/018530 | 3/2005 |

OTHER PUBLICATIONS

Gfatter et al. Dermatology. 1997;195(3):258-62.*
Machine translation of Nichiban. JP 11-049670.*
Machine translation of Showa. JP 10-316590.*
Machine translation of Ishii et al. JP 2006328059.*
Machine translation of Sekisui. JP 07-215850.*
Pharmaceutics (http://pharmlabs.unc.edu/labs/emulsions/hlb.htm; accessed Jun. 9, 2013).*
Agharkar (Journal of Pharmaceutical Sciences, vol. 65, No. 5, May 1976, pp. 747-749).*
International Search Report issued Dec. 9, 2008 in International (PCT) Application No. PCT/JP2008/003242.

* cited by examiner

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

The present invention discloses a novel tape preparation containing lidocaine at a high concentration. A tape preparation containing lidocaine at a high content, which has a lidocaine content of 10 w/w % or more, can be produced by using a lactic acid salt of lidocaine, while preventing the precipitation of a crystal of lidocaine.

8 Claims, 6 Drawing Sheets

LIDOCAINE TAPE PREPARATION

TECHNICAL FIELD

The present invention relates to a transdermal absorption preparation containing a lactic acid salt of lidocaine as a major active ingredient.

BACKGROUND ART

For lidocaine, a local anesthetic, various external preparations have previously been studied and the development of patches has progressed in recent years; several patches of lidocaine have been put on the market. To allow the anesthetic action to be exerted and improve pain in the deep part of the skin, approaches for enhancing the permeation of lidocaine into the skin are also studied; as one means therefor, patches containing lidocaine in higher concentrations are studied.

For example, Patent Document 1 discloses a tape preparation containing 20% by weight of lidocaine for the purpose of alleviating pain in centesis by an intravenous indwelling needle. Patent Document 2 discloses a preparation containing nearly 30% by weight of lidocaine. However, a high lidocaine content of about 20% by weight leads to the precipitation of a lidocaine crystal in a base of the preparation. The precipitation of the lidocaine crystal results in the dispersion of the undissolved drug in the adhesive mass; thus, in the application of the preparation to the skin or the like, a sufficient amount of the drug cannot be absorbed into the body, delaying the onset of the anesthetic effect. In addition, the problem arises that the drug remains on the skin or the like in peeling the tape preparation. The problem has also arisen that the precipitation of the drug crystal in the adhesive mass not only makes the appearance worse and but also reduces the adhesion.

Patent Document 1: Japanese Patent Laid-Open No. 2002-193795

Patent Document 2: Japanese Patent Laid-Open No. 07-215850

DISCLOSURE OF THE INVENTION

Problems to be Solved by the Invention

An object of the present invention is to provide a lidocaine-containing transdermal absorption tape preparation in which lidocaine is present in a state uniformly compatibilized with or dispersed in the base without causing the precipitation of a lidocaine crystal even when lidocaine is present in a high concentration in the preparation. Thus, because of the absence of precipitation of a lidocaine crystal, a transdermal absorption tape preparation of lidocaine which shows no deterioration of the adhesive power to the skin can be provided.

Means for Solving the Problems

As a result of intensive studies, the present inventors have found that a lactic acid salt of lidocaine (an equimolar salt) produces an ionic liquid (an ambient temperature molten salt) and have also found that formulating the ionic liquid of lidocaine into a tape preparation causes no precipitation of a lidocaine crystal in the base in the tape preparation even in a high concentration of lidocaine, and that lidocaine in the form of an ionic liquid to make the skin permeability thereof higher than otherwise. In addition, it has been shown that the use of propylene carbonate or N-methyl-2-pyrrolidone as a transdermal absorption promoting agent enhances the transdermal absorbability and tissue permeability of the ionic liquid of the lactic acid salt of lidocaine. The present inventors have completed the present invention by these findings.

Thus, the subject matters of the present invention are as follows.

[1] A lidocaine-containing nonaqueous tape preparation comprising a lactic acid salt of lidocaine, wherein the tape preparation comprises:
(1) 10 to 40 w/w % of lidocaine,
(2) lactic acid in a molar amount 0.6 to 1.2 times that of lidocaine, and
(3) propylene carbonate and/or N-methyl-2-pyrrolidone.

[2] The lidocaine-containing nonaqueous tape preparation according to item [1], further comprising a surfactant.

[3] The lidocaine-containing nonaqueous tape preparation according to item [1] or [2], wherein the surfactant comprises one or more nonionic surfactants and has an HLB value ranging from 6 to 12.

[4] The lidocaine-containing nonaqueous tape preparation according to any of items [1] to [3], wherein the tape preparation has a content of an elastomer and a tackifier of 20 to 45 w/w % as an adhesive mass layer composition thereof.

[5] The lidocaine-containing nonaqueous tape preparation according to any of items [1] to [3], wherein the tape preparation has a content of an elastomer and a tackifier of 20 to 40 w/w % as an adhesive mass layer composition thereof.

[6] The lidocaine-containing nonaqueous tape preparation according to any of items [1] to [5], wherein the elastomer in the tape preparation is a styrene-isoprene-styrene block copolymer and the tackifier is an alicyclic hydrocarbon resin.

[7] The lidocaine-containing nonaqueous tape preparation according to any of items [1] to [6], further comprising an organic acid.

[8] The lidocaine-containing nonaqueous tape preparation according to any of items [1] to [7], wherein lidocaine and lactic acid are contained in equimolar amounts.

[9] The lidocaine-containing nonaqueous tape preparation according to any of items [1] to [8], wherein the tape preparation comprises 15 to 30 w/w % of lidocaine.

[10] The lidocaine-containing nonaqueous tape preparation according to any of items [1] to [9], wherein the nonionic surfactant comprises polyoxyethylene hydrogenated castor oil and lipophilic glycerin stearate.

[11] An equimolar salt of lidocaine and lactic acid.

[12] A nonaqueous tape preparation, comprising 10 to 40 w/w % of the ionic liquid according to item [11] in terms of lidocaine.

[13] The nonaqueous tape preparation according to item [12], wherein the tape preparation comprises a nonionic surfactant comprising polyoxyethylene hydrogenated castor oil and glycerin stearate.

Advantages of the Invention

The high-concentration lidocaine tape preparation of the present invention shows no precipitation of lidocaine even when lidocaine is used in a high concentration because it uses an ionic liquid of a lactic acid salt of lidocaine. Because of this feature of the ionic liquid, many other agents including excess lidocaine are each compatibilized with the ionic liquid, resulting in no crystal precipitation. In addition, this tape preparation has an advantage that it has no unpleasant odor characteristic of a fatty acid when formulated into a tape preparation because lactic acid has low volatility unlike acetic acid and the like.

Even in a tape preparation with a high lidocaine-concentration of about 20%, the use of a lactic acid salt of lidocaine causes no precipitation of a lidocaine crystal in the base and suppresses the deterioration of adhesive power. In addition, because lidocaine is used in the form of a lactic acid salt of lidocaine, the tape preparation of the present invention is a preparation for which the transdermal absorbability of lidocaine as well as the tissue permeability thereof is stronger than for a tape preparation of lidocaine itself, enabling lidocaine to reach the deep part of the skin. In comparison with conventional transdermal absorption preparations, the preparation of the present invention is a well-balanced preparation of both the transdermal absorbability and the tissue permeability. Thus, the tape preparation of the present invention can be effectively used for the treatment of nerve pain in the deep part of the skin, cervical syndrome, migraine coming from the trigeminal nerve, and the like.

BEST MODE FOR CARRYING OUT THE INVENTION

First Aspect of Present Invention

A first aspect of the present invention relates to a lidocaine-containing nonaqueous tape preparation comprising a lactic acid salt of lidocaine as an active ingredient.

As used herein, "adhesive mass layer" relates to a composition excluding a medicinal ingredient, called a base in a tape preparation, and mainly comprises an elastomer and a tackifier, a softening agent, a filler, an antioxidant, and the like.

Examples of the "elastomer" can include synthetic rubbers such as styrene-isoprene-styrene block (hereinafter referred to as SIS) copolymer, styrene-butadiene-styrene block copolymer, styrene-ethylene-butadiene rubber-styrene block copolymer, styrene-butadiene rubber, polyisoprene, polyisobutylene, polybutene, butyl rubber, and silicon rubber, acrylic acid-based resins such as poly(acrylic acid methyl ester) and poly(methacrylic acid methyl ester), and natural rubber. Preferred are those based on rubber polymers, such as styrene-isoprene-styrene block copolymer, styrene-butadiene rubber, polybutene, polyisoprene, butyl rubber, and natural rubber. These may be used alone or in a combination of two or more thereof. The resin films may also be used alone or as a laminate of two or more thereof.

As used herein, "tackifier" refers to an alicyclic hydrocarbon resin, a polyterpene resin, an aliphatic hydrocarbon resin, a polystyrene resin, rosin, hydrogenated rosin, polybutene, and the like. Examples of preferred tackifiers can include an alicyclic hydrocarbon resin, a polyterpene resin, and polybutene.

Examples of the softening agent can include petroleum softening agents such as process oil and polybutene, fatty oil softening agents such as castor oil and coconut oil, purified lanolin, liquid paraffin, and gelatinous hydrocarbons.

Examples of the antioxidant can include dibutyl hydroxytoluene (hereinafter referred to as BHT), 4,4-dioxydiphenyl, and EDTA-2Na.

In addition, the adhesive mass may contain a transdermal absorbefacient, a surfactant (a nonionic surfactant, an anionic surfactant, a cationic surfactant, or an amphoteric surfactant), an alcohol, and an organic acid, if necessary.

The elastomer and the tackifier form the skeleton of the adhesive mass composition; thus, to prepare a preparation of a lactic acid salt of lidocaine (10 to 40 w/w % in terms of lidocaine), the total content thereof is preferably 20 to 45 w/w %. More preferred examples thereof is 20 to 40 w/w %.

When the adhesive mass is too soft, it may contain a filler. Examples of the filler include kaolin, titanium oxide, talc, calcium carbonate, magnesium carbonate, silicates, silic acid, aluminum hydrates, barium sulfate, and calcium sulfate.

The transdermal absorption promoting agent may be, for example, at least one selected from the group consisting of aliphatic monohydric alcohol esters such as isopropyl isostearate, methyl stearate, butyl stearate, butyl myristate, ethyl linoleate, isopropyl linoleate, ethyl olive oleate, myristyl myristate, cetyl isoctanoate, octyldodecyl myristate, diisopropyl adipate, cetyl palmitate, retinol palmitate, methyl laurate, methyl myristate, methyl caproate, methyl palmitate, isopropyl myristate, isopropyl palmitate, diethyl sebacate, and diethyl adipate; fatty acid polyhydric alcohol esters such as glycerin monooleate, glycerin monocaprate, glycerin dioleate, propylene glycol monostearate, and decaglycerin decaoleate; fatty acid cyclic polyhydric alcohol esters such as sorbitan monostearate, sorbitan monolaurate, sorbitan monooleate, sorbitan trioleate, and ascorbyl palmitate; cetyl lactate, myristyl lactate, n-propyl gallate, diisopropyl adipate, and propylene carbonate; and pyrrolidone derivatives such as N-methyl-2-pyrrolidone.

As a preferable transdermal absorption promoting agent, there may be used one or more selected from the group consisting of isopropyl myristate, isopropyl palmitate, diethyl sebacate, propylene carbonate, and N-methyl-2-pyrrolidone. Further, preferred examples thereof can include propylene carbonate and N-methyl-2-pyrrolidone.

As a preservative, there may be used, for example, at least one selected from the group consisting of methyl benzoate, methyl parahydroxybenzoate, ethyl parahydroxybenzoate, dodecyl parahydroxybenzoate, and the like.

Examples of the alcohol can include aliphatic alcohols such as ethanol, isopropanol, ethylene glycol, propylene glycol, 1,3-butanediol, and glycerin; and aromatic alcohols such as glycol salicylate and benzyl alcohol. Preferred examples thereof can include propylene glycol, 1,3-butanediol, and glycerin.

Examples of the organic acid can include fatty acids such as oleic acid, palmitic acid, succinic acid, lauric acid, myristic acid, stearic acid, isostearic acid, levulinic acid, decanoic acid, lactic acid, and acetic acid. These may be used alone or in a combination of two or more thereof.

Examples of the surfactant can include a nonionic surfactant, an anionic surfactant, a cationic surfactant, and an amphoteric surfactant. Examples of the nonionic surfactant include sorbitan monolaurate, sorbitan monopalmitate, sorbitan sesquioleate, glycerin monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonylphenyl ether, polyoxyethylene (7,5) nonylphenyl ether, polyoxyethylene (10) nonylphenyl ether, polyoxyethylene (3) octylphenyl ether, polyoxyethylene (10) octylphenyl ether, polyoxyethylene (10) oylelamine, polyoxy (5) oleylamine, polyoxy (5) oleic amide, polyoxyethylene (2) monolaurate, monoglyceride stearate, and polyoxyethylene castor oil (hydrogenated castor oil).

Examples of the anionic surfactant include sodium lauryl sulfate, potassium lauryl sulfate, triethanolamine lauryl sulfate, sodium cetyl sulfate, sodium lauroyl sarcosinate, sodium di-2-ethylhexyl sulfosuccinate, sodium polyoxyethylene (10) lauryl ether phosphate, sodium polyoxyethylene (4) lauryl ether phosphate, sodium polyoxyethylene (5) cetyl ether phosphate, and sodium polyoxyethylene (6) oylel ether phosphate.

Examples of the cationic surfactant include stearyl trimethylammonium chloride, distearyl dimethylammonium chloride, benzalkonium chloride, and stearyl dimethyl benzylammonium chloride.

Examples of the amphoteric surfactant include lauryldimethylaminoacetic acid betaine and 2-alkyl-N-carboxymethyl-N-hydroxyethylimidazolinium betaine. In addition to the above, lauroyl diethanolamide can also be used.

Preferred surfactants in the present invention include a surfactant having an HLB value ranging from 6 to 12. The surfactant is more preferably a surfactant containing one or more nonionic surfactants and having an HLB value ranging from 6 to 12. The nonionic surfactant is more preferably, for example, a nonionic surfactant containing monoglyceride stearate and polyoxyethylene castor oil (hydrogenated castor oil) and having an HLB value ranging from 6 to 12.

As a method for preparing the tape preparation of the present invention, methods similar to those for adhesive tapes may be adopted; examples thereof include a solvent coating method and a hot melt coating method. Examples of the solvent coating method include a method which involves preparing an base composition containing a lactic acid salt of lidocaine and the like and coating the composition directly on a backing followed by drying. A method can also be used which involves once coating the base composition on a liner followed by drying and then separating it followed by contact pressing the base to a backing.

Examples of the hot melt coating method include a method which involves heat melting the base composition and coating the composition directly on a backing before drying. For the hot melt coating method, a method can also be used which involves heat melting the base composition, once coating the base composition on a liner before drying and then separating the paper followed by transfer bonding the paper to a substrate.

The liner is used to protect the adhesive mass layer, and may use a polyethylene-coated quality paper, a polyolefin-coated glassine paper, a polyethylene terephthalate (hereinafter referred to as PET) film, a polypropylene film, or the like, one side of which is treated with silicon.

The shape of the transdermal absorption tape for local anesthesia may be freely selected from sheet, zonal, circular, elliptical, rhomboidal, and other shapes.

Second Aspect of Present Invention

A second aspect of the present invention relates to an equimolar salt of lidocaine and lactic acid.

The equimolar salt of lidocaine and lactic acid according to the present invention is a colorless, viscous liquid (an ionic liquid), and other agents including lidocaine can be dissolved in the ionic liquid.

Lidocaine has a pKa of 7.9 and lactic acid has a pKa of 3.86; because of the pKa difference of 4 or more therebetween, the equilibrium shifts to the salt side. Therefore free lactic acid can hardly be detected by IR.

The nonaqueous tape preparation comprising an equimolar salt of lidocaine and lactic acid according to the present invention means that no fatty acids are contained other than lactic acid. To achieve the object of the present invention, a transdermal absorbefacient, a surfactant (a nonionic surfactant, an anionic surfactant, a cationic surfactant, or an amphoteric surfactant), an alcohol, an antioxidant, and the like may be added, if necessary.

EXAMPLES

The present invention is more specifically described below with reference to Examples and Test Examples. However, the present invention is not intended to be limited in any manner thereby.

Example 1

Synthesis of Lactic Acid Salt of Lidocaine (Equimolar)

Figure 1:
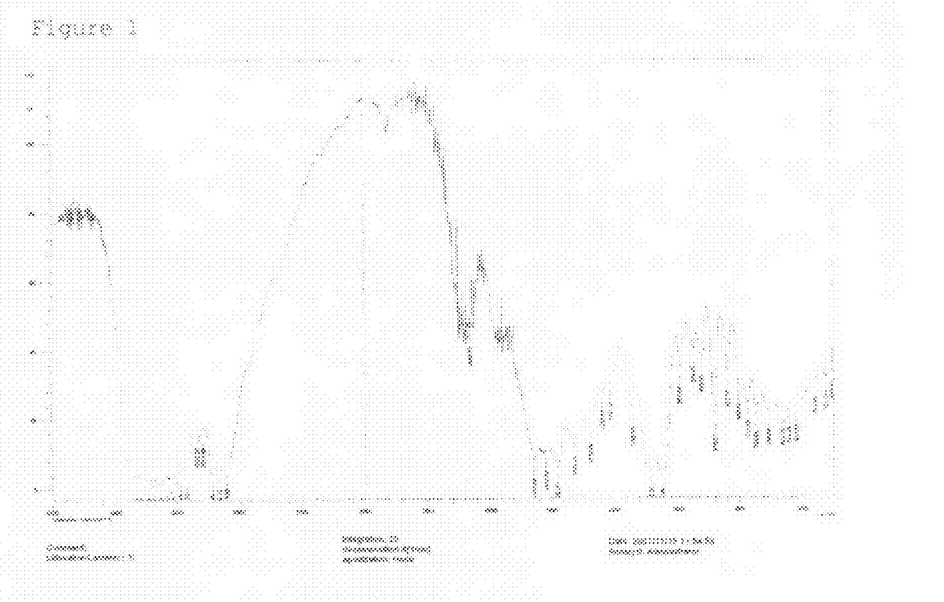
FIG. 1 is an IR absorption spectrum of a lactic acid salt of lidocaine (equimolar)

Lidocaine (15.0 g) (64.0 mM) and lactic acid (molecular sieve-dried) (5.8 g) (64.4 mM) are weighed out, mixed, and heated to about 80° C. The resultant colorless, viscous solution was taken and applied to a halite plate, and IR spectra (neat) thereof were obtained. As shown in Table 1 below, the absorption of a carboxyl group disappeared, and the absorption of a carboxyl ion appeared. The IR absorption spectra of the lactic acid salt of lidocaine is depicted in FIG. 1, and a change in the absorption position of the carboxyl group of lactic acid is shown in Table 1.

TABLE 1

| | Characteristic Absorption | |
| --- | --- | --- |
| | COOH of Lactic acid | —COO$^-$ of Lidocaine lactate (equimolar) |
| IR Absorption Position (cm$^{-1}$) | 1732 | 1680 |

[Note]
The characteristic absorption of —COO$^-$ of the lactic acid salt of lidocaine (equimolar) is shown by the median value of the absorption band, since the adsorption band was broad.

The viscous solution of the above lactic acid salt of lidocaine (ionic liquid) was allowed to stand at room temperature for several months, but no crystal precipitation occurred.

Example 2

Preparation of Tape Preparation Containing Lactic Acid Salt of Lidocaine

Tape preparations containing a lactic acid salt of lidocaine were prepared with the compositions (w/w %) described in Table 2 below. That is, SIS and terpene resin were dissolved in toluene, to which polybutene, BHT, liquid paraffin, plastibase, a surfactant, a solvent, and the like were then added and mixed under heating. After confirming the dissolution thereof, lidocaine and lactic acid were added thereto to provide a uniform base. The resultant base was coated to prepare a tape preparation.

Transdermal absorbability was measured by the method of Test Example 1 using a Franz-cell, and the transdermal absorbability ($\mu g/cm^2$) 6 hours after the start of testing was evaluated. The results are shown together in Table 2.

TABLE 2

| Samples | F262-2 | F245-1 | F213-1 |
|---|---|---|---|
| lidocaine | 10.0 (42.7 mM) | 15.0 (64 mM) | 20.0 (85.3 mM) |
| Lactic acid (90.2%) | 4.3 (43.1 mM) | 6.45 (64.6 mM) | 8.6 (86.1 mM) |
| Surfactant: | | | |
| glycerin monostearate | 0.36 | 0.36 | 0.36 |
| polyoxyethylene hydrogenated castor oil | 0.64 | 0.64 | 0.64 |
| Solvent: | | | |
| propylene carbonate | 2.0 | 2.0 | 2.0 |
| 1,3-butanediol | 2.0 | 2.0 | 2.0 |
| Softening agent: | | | |
| liquid paraffin | 19.6 | 17.45 | 24.3 |
| plastibase | 20.0 | 17.0 | 0 |
| Tackifier | | | |
| polybutene | 1.0 | 1.0 | 4.0 |
| terpene resin | 32.0 | 32.0 | 32.0 |
| Erastmer | | | |
| SIS | 8.0 | 6.0 | 6.0 |
| Antioxidant | | | |
| BHT | 0.1 | 0.1 | 0.1 |
| Total | 100.0 | 100.0 | 100.0 |
| Crystal Precipitability | None | None | None |
| Transdermal absorbability ($\mu g/cm^2$) | 127 | 151 | 204 |

Even after the storage of the 20% high-concentration lidocaine tape preparation of the above Table 2 at room temperature for several months, no precipitation of a lidocaine crystal was observed in the base. In addition, the transdermal absorbability depended on the content of lidocaine, showing a dose relationship.

Example 3

Effect of Solvent in Tape Preparation a) Effect on Transdermal Absorbability

SIS and terpene resin weighed out in the compositions described in Table 3 below were dissolved in toluene, to which polybutene, BHT, MGS, liquid paraffin, a solvent, and the like were then added and mixed under heating. Lidocaine and lactic acid (content: 90.2%) were then added thereto to provide a uniform base. The resultant base was coated, and toluene was evaporated to prepare a tape preparation.

The transdermal absorbability for the tape preparation was measured using a Franz-cell according to Test Example 1, and the transdermal absorbability ($\mu g/cm^2$) 6 hours after the start of testing was evaluated. The results are shown together in Table 3.

TABLE 3

| Sample | D395 | C404 | C405 | C406 | C407 |
|---|---|---|---|---|---|
| Lidocaine | 20.0 | 20.0 | 20.0 | 20.0 | 20.0 |
| Lactic acid (90.2%) | 10.4 | 10.4 | 10.4 | 10.4 | 10.4 |
| Surfactant: | | | | | |
| glycerin monostearate | 4.0 | 4.0 | 4.0 | 4.0 | 4.0 |
| Solvent: | — | 1,3-BG | GS | PC | NMP |
| | | 4.0 | 4.0 | 4.0 | 4.0 |
| Softening agent: | | | | | |
| liquid paraffin | 13.6 | 9.6 | 9.6 | 9.6 | 9.6 |
| Tackifier | | | | | |
| polybutene | 1.0 | 1.0 | 1.0 | 1.0 | 1.0 |
| terpene resin | 36.0 | 36.0 | 36.0 | 36.0 | 36.0 |
| Erastmer | | | | | |
| SIS | 14.0 | 14.0 | 14.0 | 14.0 | 14.0 |
| Antioxidant | | | | | |
| BHT | 1.0 | 1.0 | 1.0 | 1.0 | 1.0 |
| Crystal Precipitability | NP | NP | NP | NP | NP |
| Transdermal absorbability ($\mu g/cm^2$) | 95 | 194 | 176 | 463 | 166 |

1,3-BG: 1,3-butyleneglycol
GS: glycol salicylate
PC: propylene carbonate
NMP: N-methylpyrrolidone
NP: no precipitation According to the results in Table 3, as a solvent added to the base materials, propylene carbonate has an excellent effect. It was shown that 1,3-butanediol was a secondly good solvent.

b) Effect on Tissue Permeability

To evaluate the tissue permeability for the lidocaine tape preparations described above, each sample tape preparation was applied to a lean beef cut about 2 cm per side, which was then allowed to stand at 4° C. for 24 hours. Beef pieces were cut every 2 mm from the surface to which the sample was applied to group the pieces into three fractions 0 to 2 mm, 2 to 4 mm and 4 to 6 mm distant from the applied surface. For each fraction, the beef piece was mashed, from which lidocaine was then extracted with methanol. The concentration of lidocaine in the methanol was measured by high performance liquid chromatography.

Figure 2:
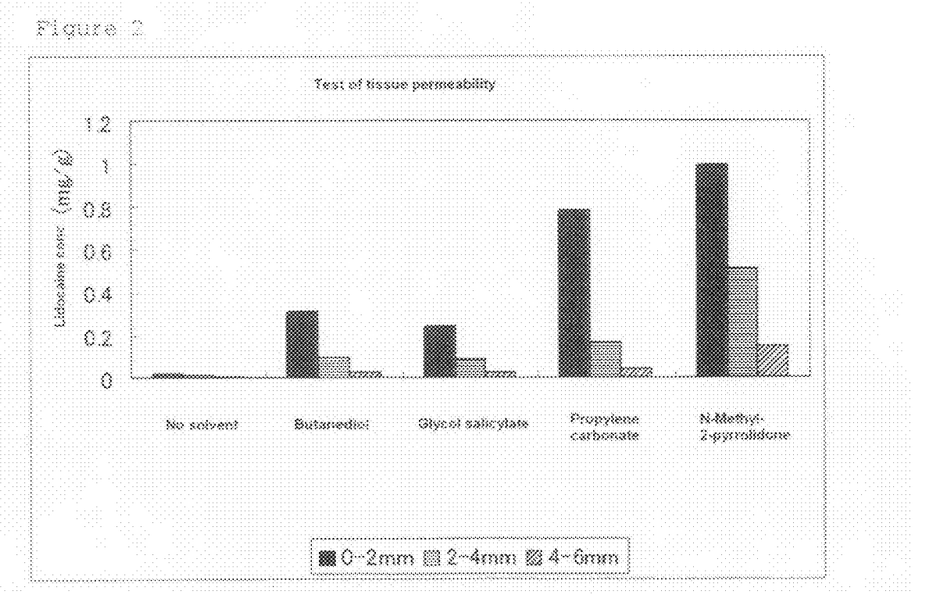
FIG. 2 is a graph showing the results of the test for evaluation of tissue permeability in Example 3.

The results are shown in FIG. 2. These results demonstrated that the lactic acid salt of lidocaine showed excellent tissue permeability when propylene carbonate or N-methyl-2-pyrrolidone was added to the base materials.

Example 4

Effect of Propylene Carbonate-Mixed Solvent System in Tape Preparation (1) Nonaqueous Tape Preparation Comprising Lactic Acid Salt of 20% Lidocaine According to the method described in Example 3a), samples were weighed out with the compositions (w/w %) of Table 4 below, and a tape preparation was prepared therefrom.

Transdermal absorbability was evaluated according to Test Example 1. The results are shown together in Table 4.

TABLE 4

| Sample | F262-1 | F213-1 | F213-2 | F213-3 |
|---|---|---|---|---|
| Lidocaine | 20.0 | 20.0 | 20.0 | 20.0 |
| Lactic acid (90.2%) | 8.6 | 8.6 | 8.6 | 8.6 |

TABLE 4-continued

| Sample | F262-1 | F213-1 | F213-2 | F213-3 |
|---|---|---|---|---|
| Surfactant: | | | | |
| glycerin monostearate | 0.36 | 0.36 | 0.36 | 0.36 |
| polyoxyethylene hydrogenated castor oil | 0.64 | 0.64 | 0.64 | 0.64 |
| Solvent: | | | | |
| propylene carbonate | 4.0 | 2.0 | 2.0 | 2.0 |
| | | BG: 2.0 | MIP: 2.0 | NMP: 2.0 |
| Softening agent: | | | | |
| liquid paraffin | 24.3 | 24.3 | 24.3 | 24.3 |
| Tackifier | | | | |
| polybutene | 4.0 | 4.0 | 4.0 | 4.0 |
| terpene resin | 32.0 | 32.0 | 32.0 | 32.0 |
| Erastmer | | | | |
| SIS | 6.0 | 6.0 | 6.0 | 6.0 |
| Antioxidant | | | | |
| BHT | 0.1 | 0.1 | 0.1 | 0.1 |
| Transdermal absorbability After 6 hours | 156 | 204 | 226 | 191 |

[Note]
BG: 1,3-Butanediol
MIP: Isopropyl Myristate
NMP: N-Methyl-2-Pyrrolidone

According to the results in the above Table 4, it was found that the combination of various solvents (transdermal promoting agents) based on propylene carbonate can enhance the transdermal absorbability. That is, the transdermal absorbability was shown to be further enhanced by adding isopropyl myristate or 1,3-butanediol to propylene carbonate to make a mixed solvent.

(2) Nonaqueous Tape Preparation Containing Lactic Acid Salt of 15% Lidocaine a) Effect on Transdermal Absorbability According to the method described in Example 3a), tape preparations of a lactic acid salt of lidocaine different in the solvent composition were prepared with the compositions (w/w %) described in Table 5 below. Transdermals absorbability was measured as described in Test Example 1. In addition, tissue permeability was measured by the method described in Example 3b).

Figure 3:
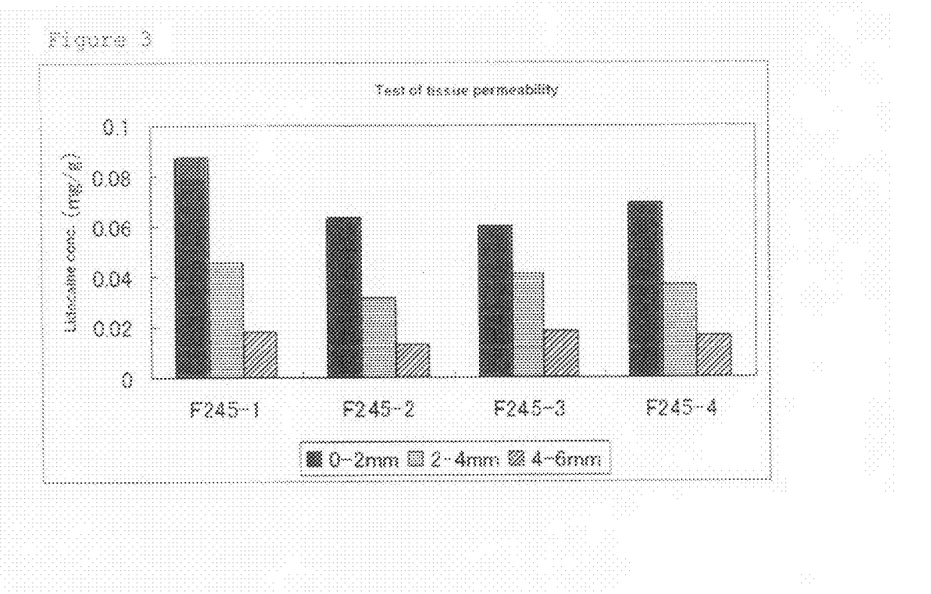
FIG. 3 is a graph showing the results of the test for evaluation of tissue permeability in Example 4.

The results of measurement of the transdermal absorbability are shown together in Table 5 below. The results of measurement of the tissue permeability are shown in FIG. 3.

TABLE 5

| Sample | F245-4 | F245-3 | F245-21 | F245-1 |
|---|---|---|---|---|
| Lidocaine | 15.0 | 15.0 | 15.0 | 15.0 |
| Lactic acid (90.2%) | 6.45 | 6.45 | 6.45 | 6.45 |
| Surfactant: | | | | |
| glycerin monostearate | 0.36 | 0.36 | 0.36 | 0.36 |
| polyoxyethylene hydrogenated castor oil | 0.64 | 0.64 | 0.64 | 0.64 |
| Solvent: | | | | |
| propylene carbonate | 0 | 0 | 2.0 | 2.0 |
| 1,3-butanediol | 0 | 2.0 | 0 | 2.0 |
| Softening agent: | | | | |
| liquid paraffin | 19.45 | 18.45 | 18.45 | 17.45 |
| plastibase | 19.0 | 18.0 | 18.0 | 17.0 |

TABLE 5-continued

| Sample | F245-4 | F245-3 | F245-21 | F245-1 |
|---|---|---|---|---|
| Tackifier | | | | |
| polybutene | 1.0 | 1.0 | 1.0 | 1.0 |
| Terpene resin | 32.0 | 32.0 | 32.0 | 32.0 |
| Erastmer | | | | |
| SIS | 6.0 | 6.0 | 6.0 | 6.0 |
| Antioxidant | | | | |
| BHT | 0.1 | 0.1 | 0.1 | 0.1 |
| Crystal Precipitability | None | None | None | None |
| Transdermal absorbability ($\mu g/cm^2$) | 190 | 169 | 190 | 151 |

The results in Table 5 above showed that the addition of propylene carbonate was preferable as a solvent in view of transdermal absorbability, while the addition of a mixed solvent of propylene carbonate and 1,3-butanediol provided more excellent permeability in view of the tissue permeability shown in FIG. 3.

As described above, it was shown that the solvent(s) not only regulated the solvation of a lactic acid salt of lidocaine and the lipid solubility of base materials, but also acted as a transdermal promoting agent and further contributed to the tissue permeability.

Thus, it was shown that a well-balanced tape preparation having the suitable transdermal absorbability and good tissue permeability of a lactic acid salt of lidocaine could be prepared by selecting various solvents, notably propylene carbonate and 1,3-butanediol, and choosing the quantitative ratios thereof.

Example 5

Effect of Addition of Surfactant in Tape Preparation a) Type of Surfactant

The effect of the presence or type of the surfactant added on the transdermal absorbability was evaluated. According to the previous section (1) a), tape preparations of a lactic acid salt of 30% lidocaine, having the compositions (w/w %) described in Table 6 below were prepared. The transdermal absorbability for each tape preparation was evaluated by using Lidoderm as a standard according to Test Example 1. The results are shown together in Table 6 below.

TABLE 6

| Sample | D270 | D271 | D262 |
|---|---|---|---|
| Lidocaine | 30.0 | 30.0 | 30.0 |
| Lactic acid (90.2%) | 10.0 | 10.0 | 10.0 |
| Surfactant: | — | HCO-60 | MGS |
| | | 0.4 | 0.4 |
| Solvent: | | | |
| 1,3-butanediol | 4.0 | 4.0 | 4.0 |
| Surfactant: | — | HCO-60 | MGS |
| | | 0.4 | 0.4 |
| Softening agent: | | | |
| liquid paraffin | 20.6 | 20.6 | 20.2 |
| Tackifier | | | |
| Alcon P-100 | 24.2 | 24.2 | 24.2 |
| polybutene | 0.4 | 0.4 | 0.4 |
| Erastmer | | | |
| SIS | 10.0 | 10.0 | 10.0 |

TABLE 6-continued

| Sample | D270 | D271 | D262 |
|---|---|---|---|
| Antioxidant | | | |
| BHT | 1.0 | 1.0 | 1.0 |
| Transdermal absorbability based on lidoderm | 1.2 | 1.8 | 2.5 |

[Note]
MGS: Monoglyceride Stearate
HCO-60: Polyoxyethylene Castor Oil

Lidoderm (registered trade name, from Endo, lidocaine content: 5%) was used as a standard material. Setting the transdermal absorbability for Lidoderm determined by a Franz-cell to 1, transdermal absorbability for each sample was indicated by relative value.

According to the results in Table 6 above, the comparison between Test Nos. D262 and D270 or the comparison between Test Nos. D271 and D270 showed that the presence of each surfactant enhanced the transdermal absorbability of lidocaine.

In addition, the use of MGS as a surfactant was shown to enhance the transdermal absorbability about 2-fold compared to that for the absence of a surfactant.

b) Combination of Surfactants

The HLB value was controlled by combining surfactants to explore the range of an HLB value suitable for a lactic acid salt of lidocaine. According to Example 3a), tape preparations having the compositions (w/w %) described in Table 7 below were prepared. According to Test Example 1, the transdermal absorbability of each tape preparation was evaluated using a Franz-cell. The results are shown together in Table 7.

TABLE 7

| Sample | C448 | C446 | C447 |
|---|---|---|---|
| Lidocaine | 20.2 | 20.2 | 20.2 |
| Lactic acid (90.2%) | 10.4 | 10.4 | 10.4 |
| Surfactant: | | | |
| HCO-60 | 2.0 | 1.0 | 0 |
| HGS | 0 | 1.0 | 2.0 |
| (HLB value) | (4) | (8) | (12) |
| Solvent: | | | |
| Propylene carbonate | 4.0 | 4.0 | 4.0 |
| Softening agent: | | | |
| liquid paraffin | 22.5 | 22.5 | 22.5 |
| Tackifier | | | |
| Terpene resin | 28.0 | 28.0 | 28.0 |
| Erastmer | | | |
| SIS | 12.0 | 12.0 | 12.0 |
| Antioxidant | | | |
| BHT | 0.1 | 0.1 | 0.1 |
| Transdermal absorbability ($\mu g/cm^2$) | 54 | 187 | 153 |

[Note]
MGS: Monoglyceride Stearate
HCO-60: Polyoxyethylene Castor Oil

Figure 4:
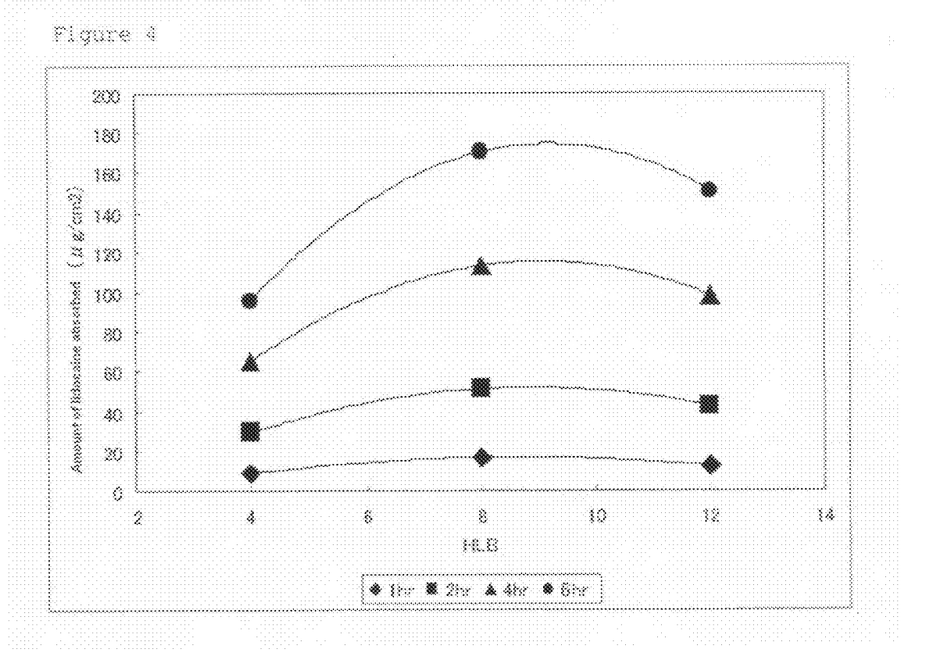
FIG. 4 is a graph showing the results of the test for evaluation of transdermal absorbability when surfactants are used in combination in Example 5.

The results in Table 7 above are illustrated in FIG. 4; at an HLB of around 8, the nonionic surfactant caused such a transdermal absorbability as to show a bell-shape maximum.

This FIG. 4 demonstrates that the HLB value of a surfactant ranged from 6 to 12 to provide more excellent transdermal absorbability.

Example 6

Crystal Precipitability of Lidocaine for High-Concentration Lidocaine Preparation The content of lidocaine was gradually increased to 40%, while the content of lactic acid was gradually decreased from equimolar to 0.65-fold molar. A content initially inducing the crystal precipitation of lidocaine was examined. According to Example 3a), tape preparations having the compositions (w/w %) described in Table 8 below were prepared. The crystal precipitability and transdermal absorbability therefor were evaluated. Lidoderm (registered trade name, from Endo, lidocaine content: 5%) was used as a standard material. Setting the transdermal absorbability of Lidoderm determined using a Franz-cell to 1, the transdermal absorbability for each sample was indicated by a relative value. The results are shown together in Table 8 below.

TABLE 8

| Sample | D261 | D267 | D263 | D264 | D265 |
|---|---|---|---|---|---|
| Lidocaine | 20.0 | 30.0 | 30.0 | 35.0 | 40.0 |
| Lactic acid (90.2%) | 7.7 | 11.6 | 10.0 | 10.0 | 10.0 |
|  | equi-molar | equi-molar | 0.86-fold Molar | 0.74-fold Molar | 0.65-fold Molar |
| Surfactant: | | | | | |
| MGS | 0.4 | 0.4 | 0.4 | 0.4 | 0.4 |
| Solvent: | | | | | |
| 1,3-butanediol | 4.0 | 4.0 | 4.0 | 4.0 | 2.0 |
| Softening agent: | | | | | |
| liquid paraffin | 18.5 | 18.6 | 22.2 | 20.2 | 19.2 |
| Tackifier | | | | | |
| Polybutene | 0.4 | 0.4 | 0.4 | 0.4 | 0.4 |
| Alcon P-100 | 38.0 | 24.0 | 24.0 | 22.0 | 20 |
| Erastmer | | | | | |
| SIS | 10.0 | 1.0 | 18.0 | 7.0 | 7.0 |
| Antioxidant | | | | | |
| BHT | 1.0 | 1.0 | 1.0 | 1.0 | 1.0 |
| Crystal Precipitability | None | None | None | None | None |
| Transdermal absorbability based on lidoderm | — | 3.9 | 2.3 | — | — |

[Note]
MGS: Monoglyceride Stearate

According to the results in Table 8 above, the crystal precipitation of lidocaine was not observed even when the content of lidocaine reached 40%. This result may be largely due to the physical properties of the lactic acid salt of lidocaine (ionic liquid). That is, because the lactic acid salt of lidocaine was an ionic liquid, lidocaine was not observed to precipitate as a crystal even when reaching the high concentration. In addition, even when lidocaine is in considerable excess relative to lactic acid, lidocaine is dissolved in the ionic liquid of the lactic acid salt of lidocaine and its crystallization is depressed.

Even for the 40% high-concentration preparation, the adhesion of the tape preparation to the skin was still favorable with little change. When the concentration of lidocaine becomes high and its crystal is thereby precipitated, the adhesion is generally reduced. This is prevented for the preparation of the present invention; thus, the effect on the adhesion is reduced.

Example 7

Effect of Lactic Acid Salt of Lidocaine on Tissue Permeability

A known reference (Abstract of WO01/07018) describes that sodium acetate is suitable as a transdermal absorption promoting agent for acid addition salts of basic drugs. Example 3 in the known reference describes a tape preparation containing 15% oxybutynin hydrochloride as an active ingredient; Test Example 1 therein describes that the formula of a tape preparation in Example 3 is most excellent in the skin permeability of the ingredient. That is, according to the known reference, it is expected that oxybutynin acetate is generated in the system and gives an excellent skin permeability.

Accordingly, a tape preparation having the above formula in which oxybutynin hydrochloride was replaced with lidocaine hydrochloride (a tape preparation of an acetic acid salt of lidocaine) was prepared, and compared with a preparation of the present invention (a tape preparation of a lactic acid salt of lidocaine).

It follows that the use of 15% of lidocaine hydrochloride results in the formula of a preparation containing 13% of lidocaine. Thus, the above-described tape preparations were prepared with the compositions (w/w %) described in Table 9 below.

Figure 5:
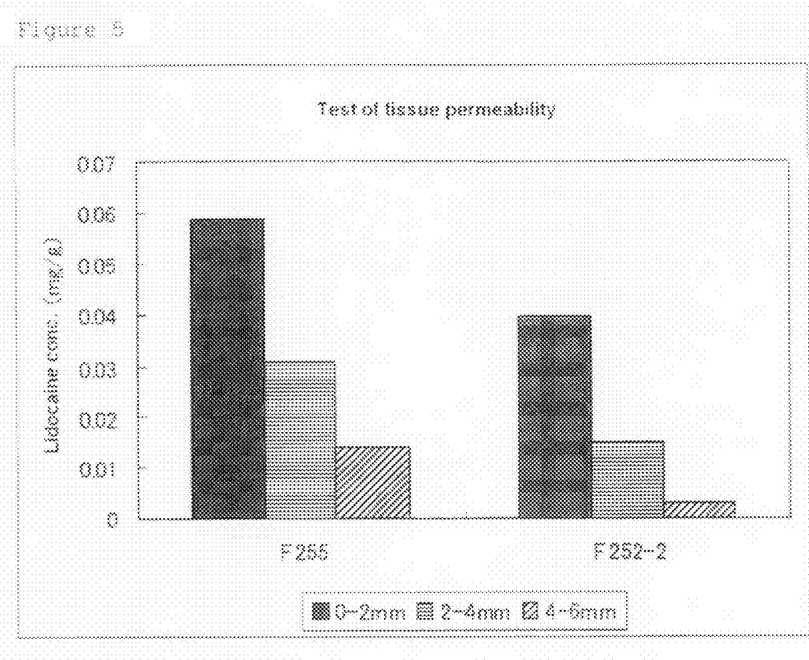
FIG. 5 is a graph showing the results of the test for evaluation of tissue permeability in Example 7.

Transdermal and tissue permeability were evaluated according to Example 3, and the results are shown in Table 9 and FIG. 5.

TABLE 9

| Sample | F252.2 a) | F255 b) |
|---|---|---|
| Lidocaine | Lidocaine HCl: 15.0(55.4 mM) | Lidocaine: 13.0(55.5 mM) |
| Organic acid/Organic acid salt | Sodium acetate * 9.0(66.1 mM) | Lactic acid(90.2%) 5.6(56.1 mM) |
| Surfactant: | | |
| glycerin monostearate | 0 | 0.36 |
| polyoxyethylene hydrogenated castor oil | 0 | 0.64 |
| Solvent: | | |
| propylene carbonate | 0 | 2.0 |
| 1,3-butanediol | 0 | 2.0 |
| Softening agent: | | |
| liquid paraffin | 10.5 | 17.3 |
| plastibase | 0 | 18.0 |
| Tackifier | | |
| hydrophobic polymer tackifier resin | Polyisobutylene: 13.0 Alcon P-100: 32.0 | Polybutene: 1.0 Terpene resin: 32.0 |
| Erastmer | | |
| SIS | 18.0 | 8.0 |
| Antioxidant | | |
| BHT | 0 | 0.1 |
| Transdermal absorbability (μM/cm²) | 131 | 184 |

\* Japanese Pharmacopoeia
a) Prior Art Reference
b) Present Invention

The above Table 9 showed that the transdermal absorbability for the preparation of the present invention was about 1.5-fold better than that for the preparation F252-2 based on the prior art reference.

In addition, the results in FIG. 5 shows that the tissue permeability for the preparation of the present invention was about 4-fold better in a deep tissue 4 to 6 mm in depth than that for the preparation F252-2 based on the prior art reference.

As described above, it was shown that the tape preparation of the present invention was excellent and well-balanced in both transdermal absorbability and tissue permeability compared to that for the preparation based on the prior art reference.

Example 8

Effect of Other Additive in Tape Preparation

The composition of lidocaine, lactic acid, and the like was fixed, and the effect of addition of other additive on the transdermal absorbability was evaluated. To this end, tape preparations having the compositions (w/w %) described in Table 10 below were prepared according to Example 3. The crystal precipitability and transdermal absorbability were evaluated, and the results are shown together in Table 10 below. The transdermal absorbability was given by the relative evaluation using Penles as a standard.

TABLE 10

| | Sample | | | | |
|---|---|---|---|---|---|
| | Ref. Example (D275) | D269 | D284 | D295 | D296 |
| Lidocaine | 30.0 | 30.0 | 30.0 | 30.0 | 30.0 |
| Lactic acid (90.2%) | — | 10.0 | 10.0 | 10.0 | 10.0 |
| Surfactant: | | | | | |
| MGS | 0.4 | 0.4 | 0.4 | 0.4 | 0.4 |
| Solvent: | | | | | |
| 1,3-butanediol | — | — | 4.0 | — | — |
| Organic acid | | | | | |
| Isostearic acid | — | — | — | 2.8 | 2.8 |
| Oranic base | | | | | |
| diisopropanolamine | — | — | — | 6.0 | 6.0 |
| Softening agent: | | | | | |
| liquid paraffin | 34.2 | 34.2 | 34.2 | 34.2 | 34.2 |
| Tackifier | | | | | |
| polybutene | 0.4 | 0.4 | 0.4 | 0.4 | 0.4 |
| Alcon P-100 | 24.0 | 24.0 | — | 24.0 | 24.0 |
| Erastmer | | | | | |
| SIS | 10.0 | 10.0 | 20.0 | 10.0 | 12.0 |
| Antioxidant | | | | | |
| BHT | 1.0 | 1.0 | 1.0 | 1.0 | 1.0 |
| Crystal Precipitability | CP | NP | NP | NP | NP |
| Transdermal absorbability Based on Penles | 1.1 | 1.7 | 1.5 | 2.2 | 2.1 |

NP: No precipitation
CP: Crystal precipitation
[Note]
MGS: Monoglyceride Stearate
Penles (registered trade name, from Yutoku, lidocaine content: 10%) was used as a standard material. Setting the transdermal absorbability determined employing a Franz-cell using Penles to 1, the transdermal absorbability for each tape preparation is indicated by a relative value.

Table 10 above shows that the presence of lactic acid makes a great difference in the transdermal absorbability. As shown in the reference example (D275) and Test No. D295, the presence of lactic acid enhanced the transdermal absorbability about 2-fold.

Test Example 1

Evaluation Test of Transdermal Absorbability Using a Franz-Cell

Figure 6:
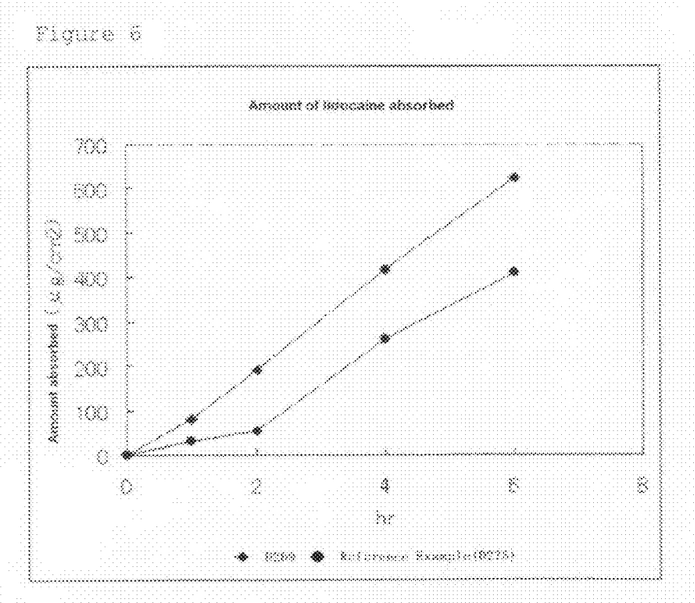
FIG. 6 is a graph showing the results of the test for evaluation of transdermal absorbability for the tape preparation in Test Example 1.

Five-week old Wistar rats were used. The hair of the abdomen was removed using a hair clipper and a shaver on the day prior to the test, and an abdominal skin was removed after euthanasia with ether. The abdominal skin is mounted in a vertical diffusion cell (effective diffusion area: 1 cm$^2$), and the tapes of the above Examples, cut to the same size, are each applied to the stratum corneum side thereof. In addition, physiological saline was applied to the dermic layer side. The experimental temperature was set at 32° C. The physiological saline (300 μL) was sampled 2, 4, and 6 hours after the start of the experiment, and measured by HPLC for the concentration of lidocaine eluted by passing through the skin to determine the cumulative permeation amount of lidocaine at each time. The results of the reference example (D275) and Test No. 269 were shown in FIG. 6.

Test Example 2

Evaluation Test of Permeability Using Meat Piece

Figure 7:
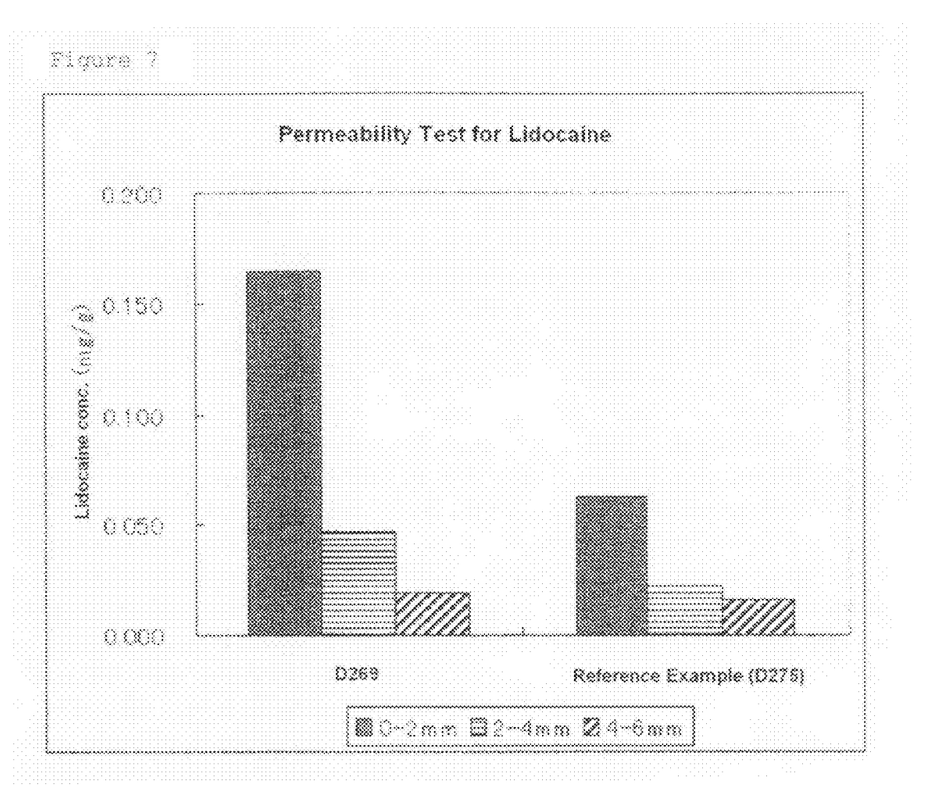
FIG. 7 is a graph showing the results of the test for evaluation of diffusion for the tape preparation into a beef tissue in Test Example 2.
Figure 8:
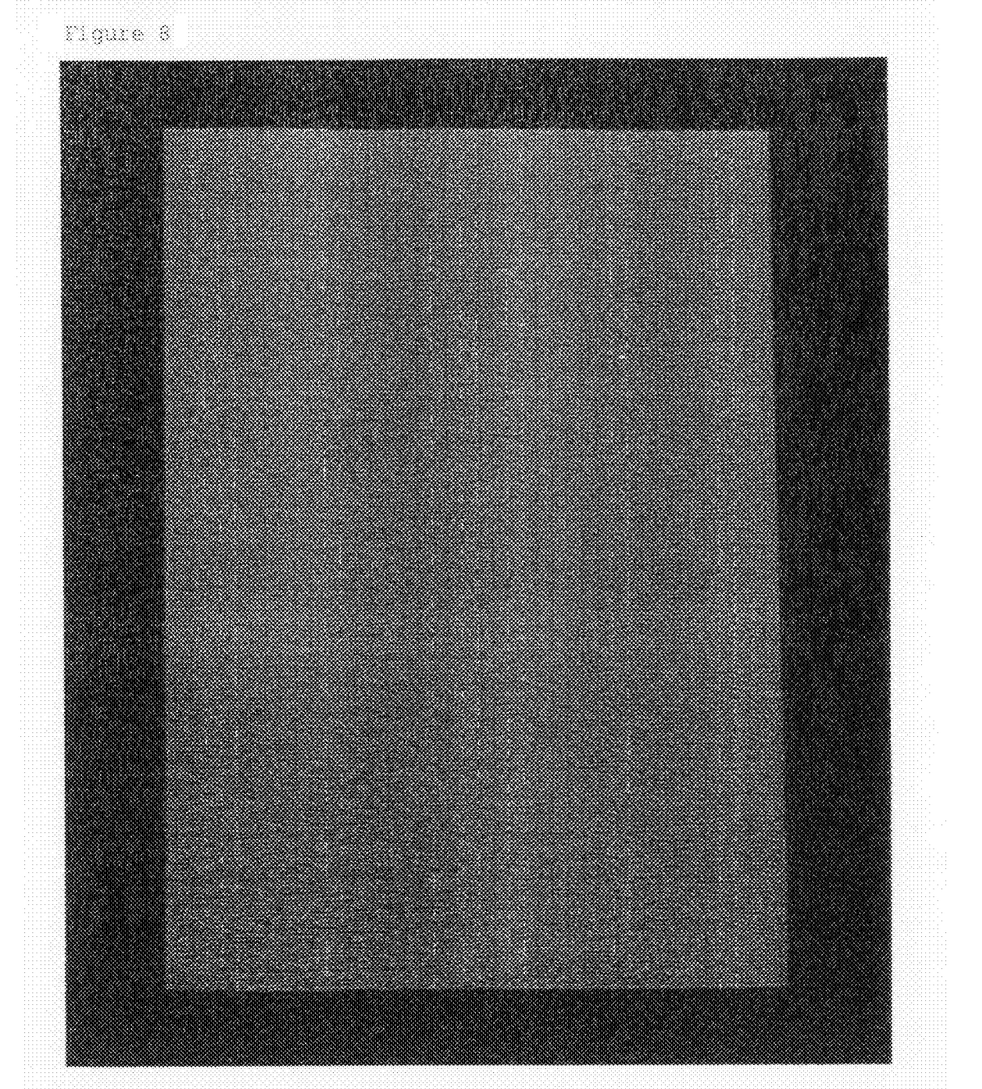
FIG. 8 is a photograph of the outer shape of the tape preparation of Test No. 269 (absence of crystal precipitation)
Figure 9:
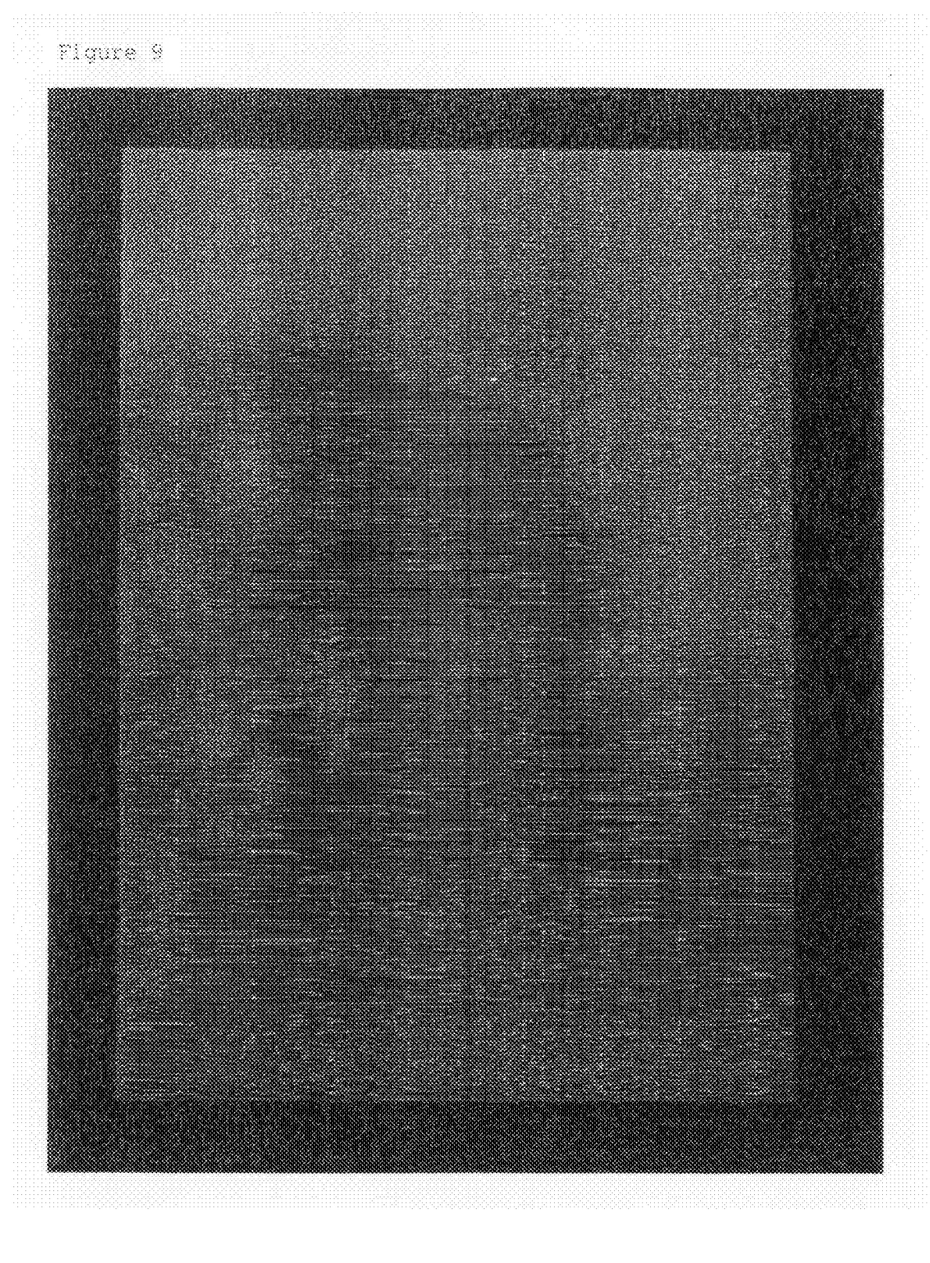
FIG. 9 is a photograph of the outer shape of the tape preparation of a reference example (D275) (presence of crystal precipitation).

Each sample tape preparation was applied to a lean beef cut about 2 cm per side, which was then allowed to stand at 4° C. for 24 hours. Meat pieces were cut every 2 mm from the surface on which the sample was applied to group the pieces into three fractions 0 to 2 mm, 2 to 4 mm and 4 to 6 mm distant from the applied surface. For each fraction, the meat piece was mashed, from which lidocaine was then extracted with methanol. The concentration of lidocaine in the methanol was measured by high performance liquid chromatography. The results of the reference example (D275) and Test No. 269 are shown in FIG. 7.

Test Example 3

Ball Tack Test

According to JIS Z 0237 "adhesive tape/adhesive sheet test method" (14 "slope-type ball tack test"), the tape preparations of D262 (a lactic acid salt of lidocaine) of Example 5 and D275 (no lactic acid) of Example 8 were used to perform an evaluation test. Each tape preparation is placed with the adhesive side up on a slide having an angle of inclination of 30°. A number 4 ball was placed on the surface of the adhesive side; the halt of the ball for 60 seconds or more after the placement was evaluated as "good" and the rolling-down thereof in 60 seconds thereafter, as "poor."

The experiment was performed three times. As a result, the ball halted for 60 seconds or more in each experiment for D262 (a lactic acid salt of lidocaine), whereas only the halt time of less than 60 seconds were obtained for D275 (no lactic acid).

INDUSTRIAL APPLICABILITY

The lidocaine tape preparation of the present invention is a nonaqueous tape preparation which contains a lactic acid salt of lidocaine as an active ingredient and further in which propylene carbonate or N-methyl-pyrrolidone is used as a solvent and combined with various solvents and a surfactant is added. Because of the composition described above, the preparation causes no crystal precipitation even when it is a formula of a preparation containing a high concentration of lidocaine and also is excellent and well-balanced in the transdermal absorbability and tissue permeability of lidocaine. Thus, the lidocaine tape preparation of the present invention can be effectively used for the treatment of nerve pain in the deep part of the skin, cervical syndrome, migraine coming from the trigeminal nerve, and the like.

The invention claimed is:

1. A lidocaine-containing nonaqueous tape preparation comprising an ionic liquid of a lactic acid salt of lidocaine, wherein the ionic liquid is an ambient temperature molten salt and the tape preparation comprises:
   (1) 10 to 40 w/w % of lidocaine,
   (2) lactic acid in a molar amount 0.6 to 1.2 fold that of lidocaine,
   (3) propylene carbonate,
   (4) a surfactant, and
   (5) 20 to 45 w/w % of an elastomer and a tackifier.

2. The lidocaine-containing nonaqueous tape preparation according to claim 1, wherein the surfactant comprises one or more nonionic surfactants and has an HLB value ranging from 6 to 12.

3. The lidocaine-containing nonaqueous tape preparation according to claim 1, further comprising an organic acid.

4. The lidocaine-containing nonaqueous tape preparation according to claim 1, wherein lidocaine and lactic acid are contained in equimolar amounts.

5. The lidocaine-containing nonaqueous tape preparation according to claim 1, wherein the tape preparation comprises 15 to 30 w/w % of lidocaine.

6. The lidocaine-containing nonaqueous tape preparation according to claim 1, wherein the surfactant comprises polyoxyethylene hydrogenated castor oil and glycerin stearate.

7. An equimolar salt of lidocaine and lactic acid which is an ionic liquid that is an ambient temperature molten salt.

8. A nonaqueous tape preparation, comprising 10 to 40 w/w % of the equimolar salt according to claim 7 in terms of lidocaine.

* * * * *